United States Patent [19]

Norman

[11] 4,144,460
[45] Mar. 13, 1979

[54] METHOD AND DEVICE FOR RADIOGRAPHING HUMAN JAW JOINTS

[75] Inventor: Royal L. Norman, Omaha, Nebr.

[73] Assignee: Rinn Corporation, Elgin, Ill.

[21] Appl. No.: 830,413

[22] Filed: Sep. 6, 1977

[51] Int. Cl.² ............................................. G03B 41/16
[52] U.S. Cl. .................................... 250/451; 250/468
[58] Field of Search ............ 250/468, 451, 456, 439 R, 250/491

[56] References Cited

U.S. PATENT DOCUMENTS

| | | | |
|---|---|---|---|
| 2,903,588 | 9/1959 | Mennech | 250/491 |
| 3,154,683 | 10/1964 | Blair | 250/451 |
| 3,777,140 | 12/1973 | Graf | 250/451 |
| 3,864,563 | 2/1975 | Hozumi | 250/491 |
| 3,930,164 | 12/1975 | Alexander | 250/468 |

*Primary Examiner*—Craig E. Church
*Attorney, Agent, or Firm*—McWilliams, Mann & Zummer

[57] ABSTRACT

A method and device for radiographing the human jaw joints for providing a clear image of one of the joints on one dental film and for providing a clear image of the other joint on a separate second dental film, comprising a frame equipped for mounting the respective films on either side of the patient's head, with the respective film holders of the frame and an X-ray positioning target for each such holder being arranged in sets oriented to be coordinated with the patient's Ala-tragal plane, in which the film holder of each set is disposed adjacent the jaw joint to be radiographed and the target therefor is disposed on the other side of the patient's head on an X-ray axis that is to pass through the joint the particular film is to bear, which axis is oblique to a straight line connecting the jaw joints to be radiographed. The frame is arranged for comfortable three point support on the patient's head by being applied to the external auditory meatus of each of the patient's ears and braced elsewhere on the patient's head. The frame is also arranged to be referred to the patient's Ala-tragal plane for coordinating the film holder-target sets with the jaw joints to be radiographed.

17 Claims, 11 Drawing Figures

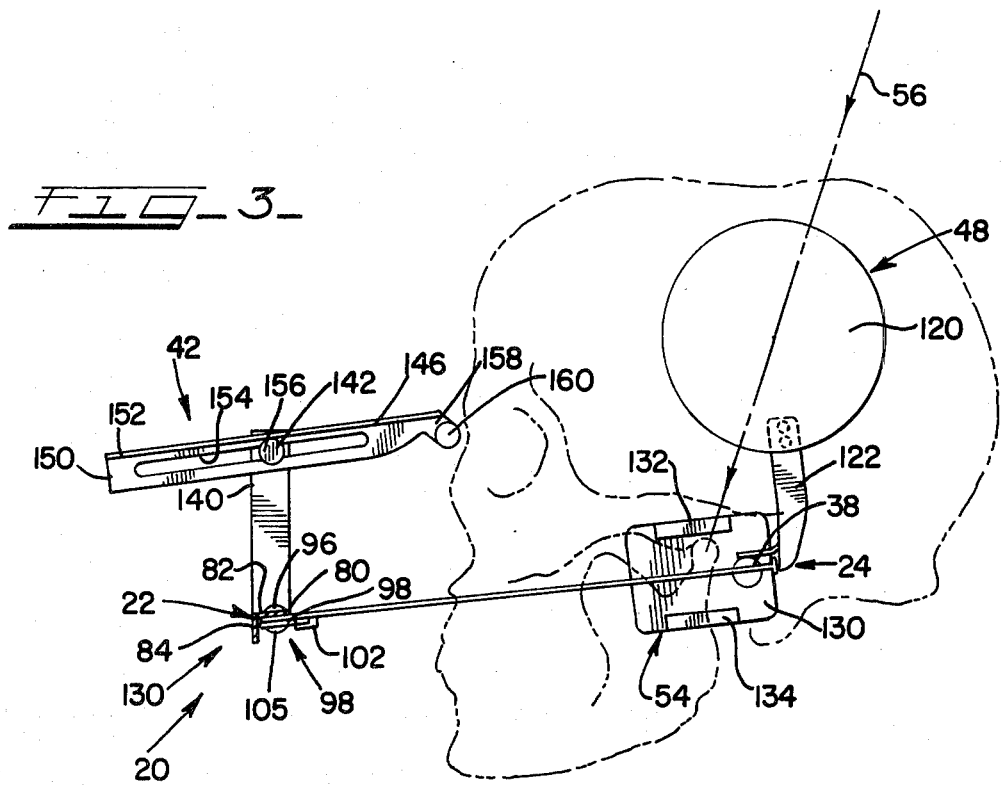
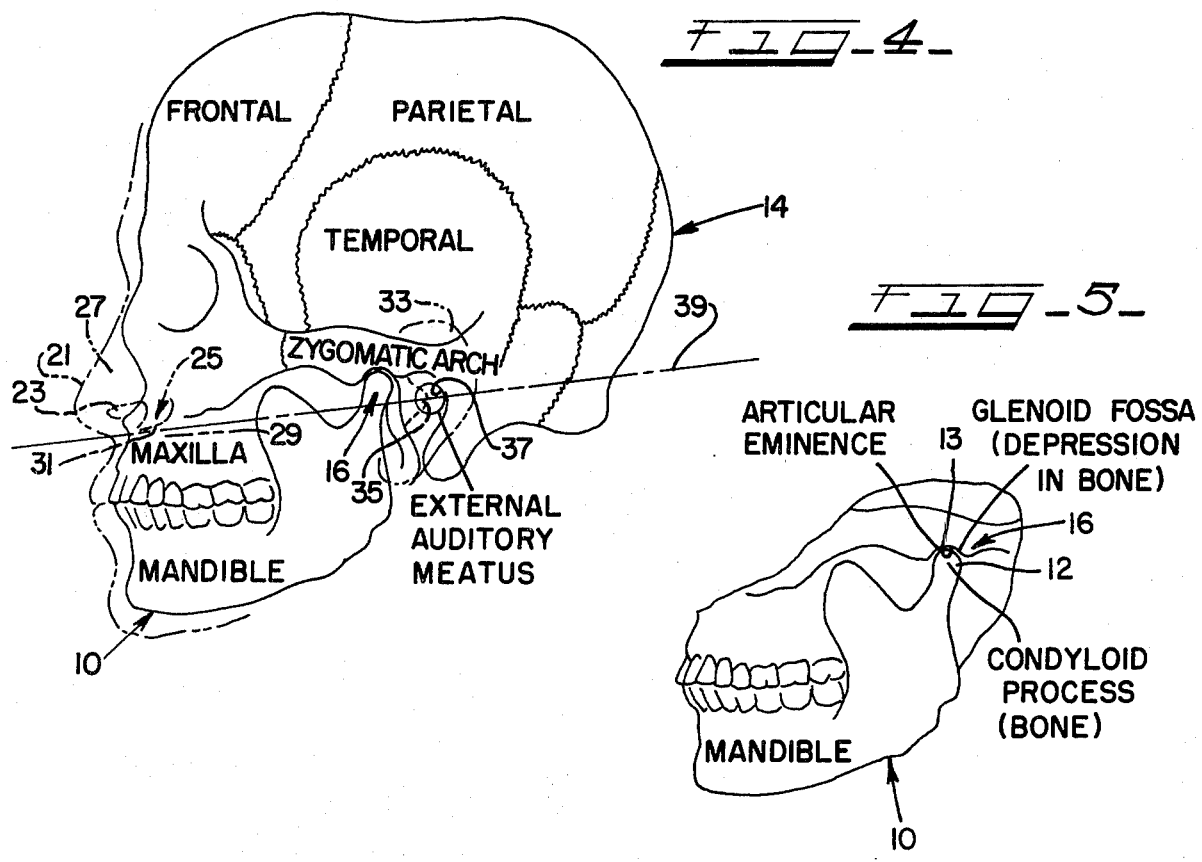

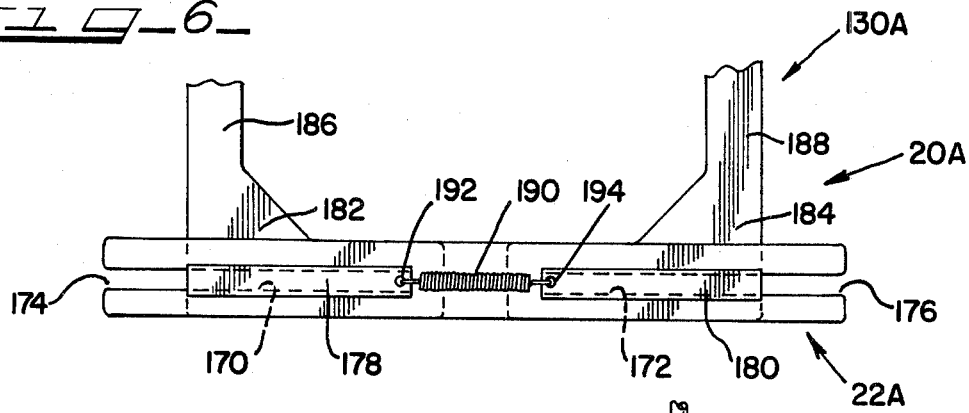
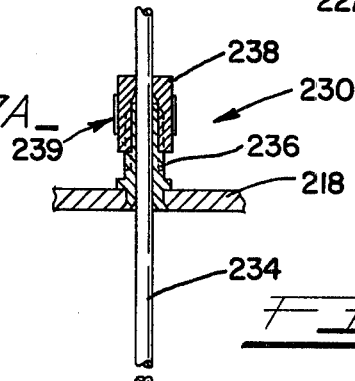
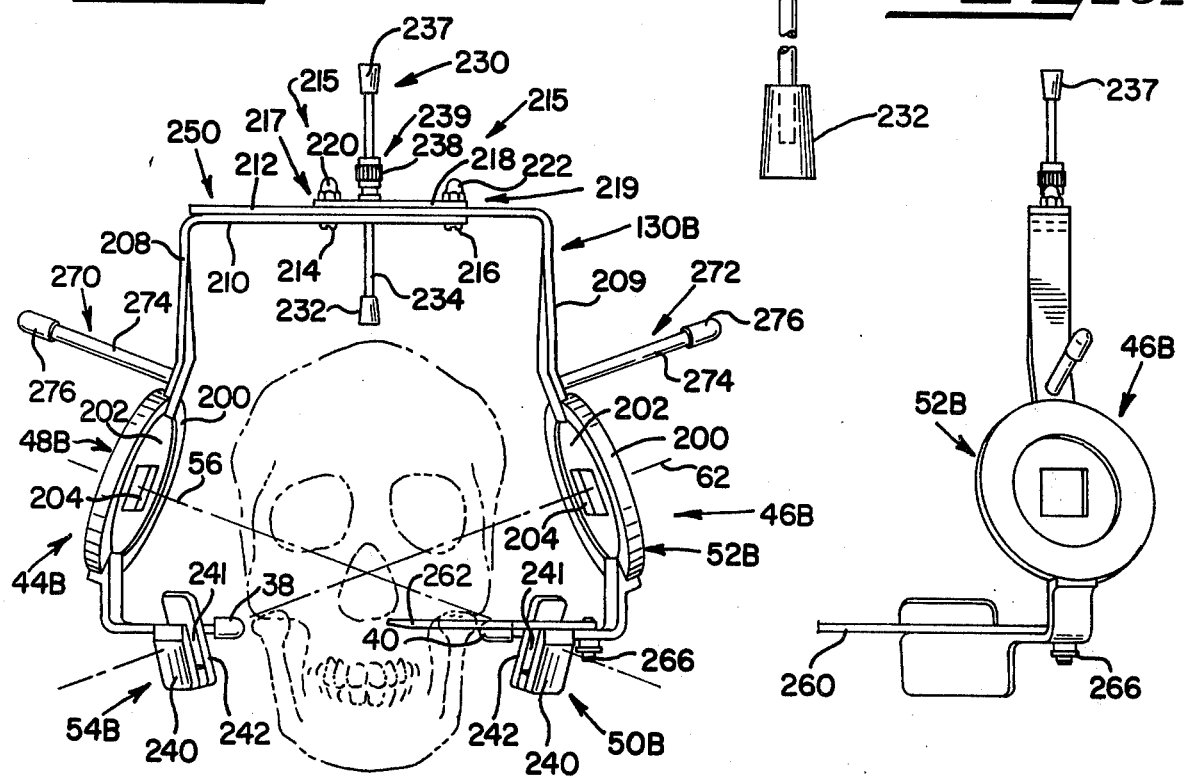

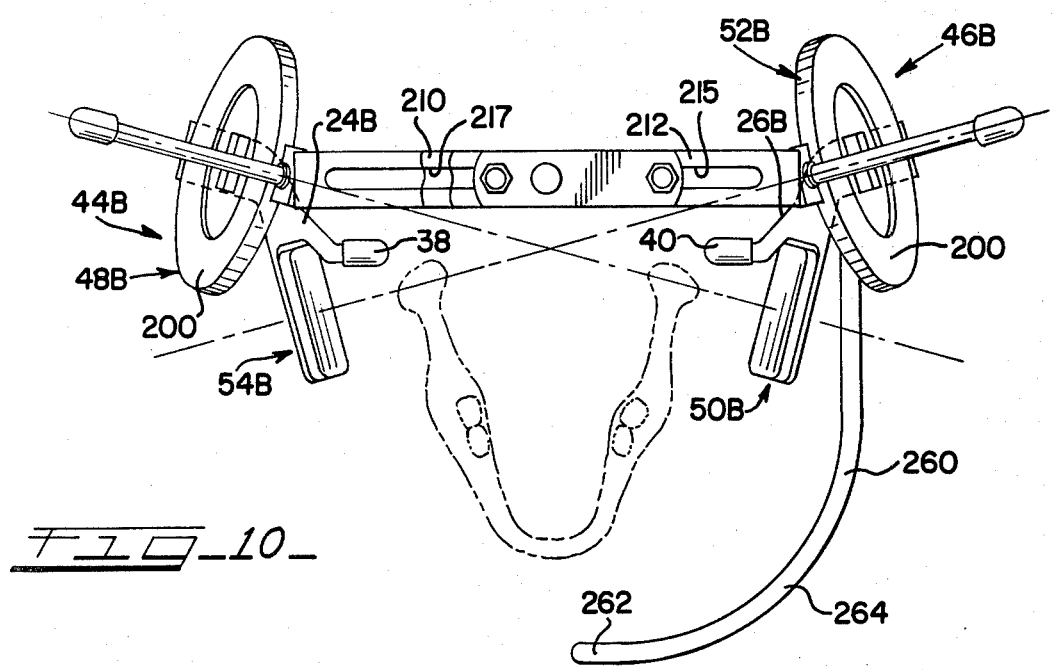
FIG_10_
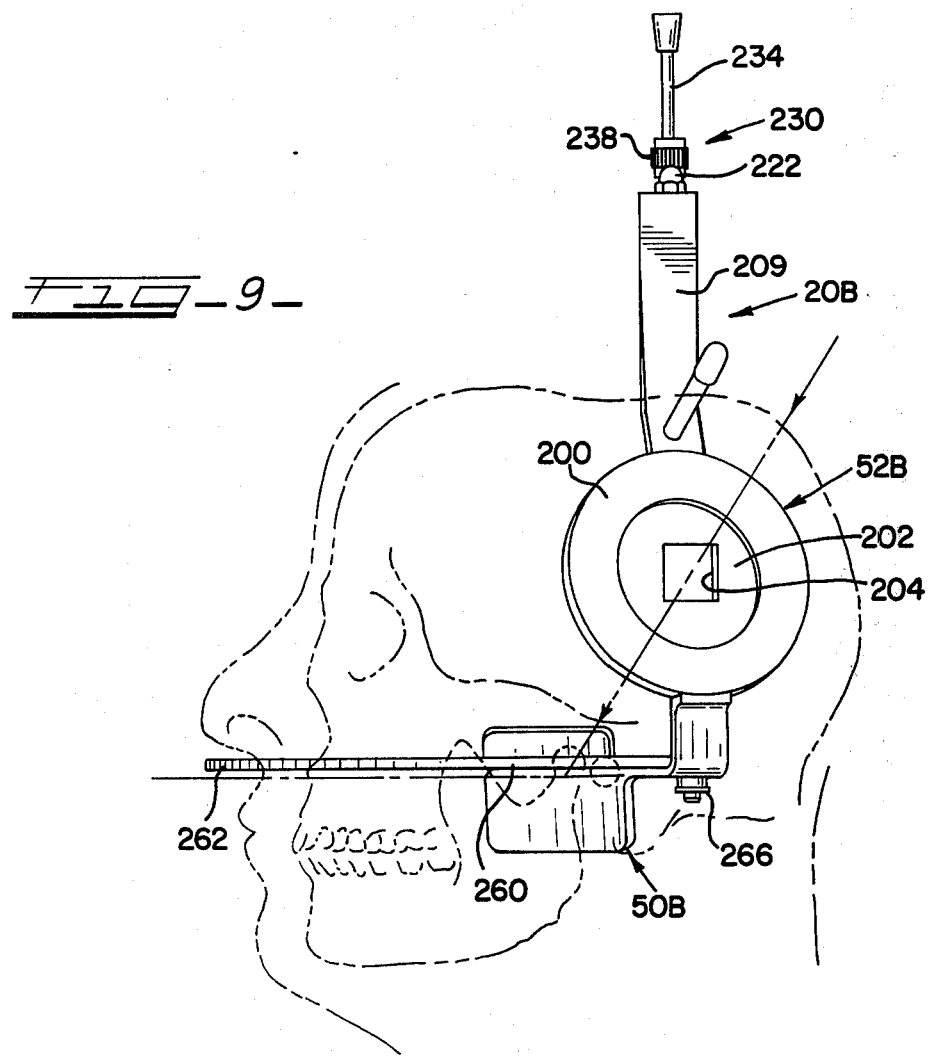
FIG_9_

METHOD AND DEVICE FOR RADIOGRAPHING HUMAN JAW JOINTS

This invention relates to a method and device for radiographing the temporomandibular joints of a patient's head, and more particularly, to a film and X-ray coordination device and method of using same for obtaining consistently good diagnostic X-ray film images of the patient's temporomandibular joints using standard dental office X-ray equipment, film of dental X-ray size, and dental film developing equipment and procedures.

The human lower jaw or mandible is hinged to the temporal bone of the skull on both sides of the skull just in front of the ears. This hinge or joint is referred to as the temporomandibular articulation or joint, which for convenience of description shall hereinafter be referred to as the TMJ.

While there are many reasons for radiographing the TMJ, a particularly significant problem for dentists is that should dental work done on the patient, such as fillings and the like, result in even minor projections or protrusions above the normal tooth engagement level that would block or impede normal occlusion when the patient's jaws are brought together, one or both of the patient's TMJs may be thrown out of line on occlusion. Over a period of time, this can develope into an extremely painful condition. Diagnosis and treatment can be greatly enhanced with the availability of good X-ray film images of the patient's TMJ articulations.

Existing techniques for radiographing the TJM are less than satisfactory for many reasons. Equipment and practices employed require a substantial investment in both equipment and highly trained technicians, yet results are all too frequently indeterminate and inaccurate. Furthermore, available equipment is cumbersome to operate and most techniques require the patient to assume an uncomfortable and awkward position of the head to practice and techniques involved. Some of the problems and proposed improvements in TMJ radiology techniques are discussed in the paper by Dr. Lawrence A. Weinberg entitled "Technique for Temporomandibular Joint Radiographs", which appeared in the Journal of Prosthetic Dentistry, Volume 30, No. 6.

While from cost and technology standpoints, TMJ radiology has been for all practical purposes out of range of many dental practices, and the patient discomforture involved has tended to discourage use of existing TMJ radiology techniques, the fact remains that good TMJ diagnostic X-ray film images can alert the dentist to TMJ problems that can lead to major patient discomfurture unless promptly corrected. This is because TMJ displacement is readily apparent from good TMJ diagnostic X-ray film images where conditions impeding normal occlusion exist.

A principal object of this invention is to provide a method and device for making TMJ X-ray film images using standard X-ray equipment that the dentist would ordinarily have available in his office, and without requiring special office or laboratory facilities.

Another principal object of the invention is to provide TMJ radiology techniques and an X-ray film holding device for use in connection therewith that requires no special training to operate and permits the use of periapical size film for TMJ radiology purposes.

Still another principal object of the invention is to provide a dental X-ray film-beam coordinating device for TMJ radiology that involves no patient discomforture or awkward positioning in use, that is applied to the patient while sitting or standing in a normal upright manner, and that provides for reproducability of X-ray images at the same position at subsequent dates.

Another important object of the invention is to provide a TMJ X-ray coordinating device suitable for everyday dental practice which integrates, in one piece of light-weight equipment, a film holder and X-ray beam locater set for each of the patient's TMJ articulations to be radiographed, with each such set being mounted on the patient's head and coordinated with reference to the patient's TMJ articulations by application to the patient's external auditary meatus and referenced to a constant facial reference plane for making substantially automatic correct film positioning relative to the patient's respective TMJs, on application of the device to the patient, that will insure good diagnostic TMJ X-ray images on a routine basis.

Yet other important objects of the invention are to provide a simple TMJ film holder device that requires no special training to operate, that is suitable for incorporation in the practicing dentist's routine procedures, that achieves maximum precision while accommodating some adjustment due to variations in head sizes and shapes, and that is economical of manufacture, convenient to use, and long lived in operation.

In accordance with the invention, a film holder and X-ray target equipped frame is provided that is arranged for support on the patient's head by application to the external auditary meatus of the patient's ears and bracing elsewhere against the patient's head for a firm three point support on the patient's head without inducing patient discomfiture.

The frame includes a base portion having associated with same a pair of film holders and an X-ray positioning target for each, in which the holders and targets are arranged in a pair of sets, in which the respective film holders are disposed, when the device is applied in its operating position to the patient's head, adjacent the TMJ to be radiographed onto a particular film, and the positioning target therefor is disposed on the other side of the patient's head on an X-ray axis that is to pass through the joint that is to be imaged on the particular film in question and be oblique to a straight line connecting the patient's TMJs.

The film and X-ray beam locating target of each TMJ radiographing set are mounted on the frame on separate opposed mounting members respectively connected to the frame for adjustment toward and away from each other, with the mounting members each being equipped with an applicator for applying same to the external auditary meatus of the patient's ears. The mounting members are positionally maintained by their connections with the frame to keep the respective film holder and target sets properly oriented relative to each other while accommodating adjustment for variations in head size and shape. The frame is arranged to be referenced to the patient's Ala-tragal plane to coordinate the film holder and target sets with the patient's TMJ's, and includes a rest or seat for engagement with the patient's head at a position spaced from but between his ears for providing the aforementioned three point support for the device.

The device is applied to the patient's head by inserting the mounting member applicators in the external auditary meatus of the patient's ears, with the device base portion disposed crosswise of the patient's head.

The frame is referenced to the patient's Ala-Tragal plane and engaged with the patient's head at the indicated third point of support to cooridinate the frame holder and target sets with the patient's TMJ's. In this position, the device is ready for use in connection with the dentist's conventional dental X-ray beam generating and emitting apparatus. The patient, in accordance with the invention, remains in a normal upright position, whether sitting or standing, in using the device, and the X-ray apparatus PID is sequentially aligned with the X-ray axes defined by the respective TMJ radiographing sets provided by the coordinating device, for sequential making of X-ray images on the respective films carried by the device.

The device is arranged to be readily reapplied to the same setting at a later date for subsequent making of X-ray images at the same locations with reference to the patient's TMJ's.

The film holders of the device are arranged to hold standard Periapical size film packets, which when exposed may be processed in the usual manner utilizing the dentist's standard film processing equipment and procedures to provide the needed TMJ images.

Other objects, uses and advantages will be obvious or become apparent from a consideration of the following detailed description and the application drawings, in which like reference numerals indicate like parts throughout the several views.

In the drawings:

FIG. 3 is a sectional view taken substantially along line 3—3 of FIG. 2, again showing the human skull in outline for the same purpose;

FIGS. 4 and 5 are representations of the left side of the human skull and jaw bone, illustrating the jaw articulation or joint that is to be radiographed in accordance with this invention, and showing in phantom associated portions of the human nose, mouth and ear;

FIG. 6 is a fragmental view of a modification of the embodiment of FIGS. 1-3, being a bottom plan view of the frame base portion and associated parts;

FIG. 7 is a view similar to that of FIG. 2, illustrating another embodiment of the invention;

FIG. 7A is a fragmental elevational view, partially in section, and on an enlarged scale, of the head rest device shown in FIG. 7;

FIG. 8 is a view similar to that of FIG. 3, showing the embodiment of FIG. 7;

FIG. 9 is a view similar to that of FIG. 3, showing the device of FIGS. 7 and 8 as applied to the patient; and FIG. 10 is a top plan view of the device as shown in FIG. 7, with parts broken away.

Figure 1:
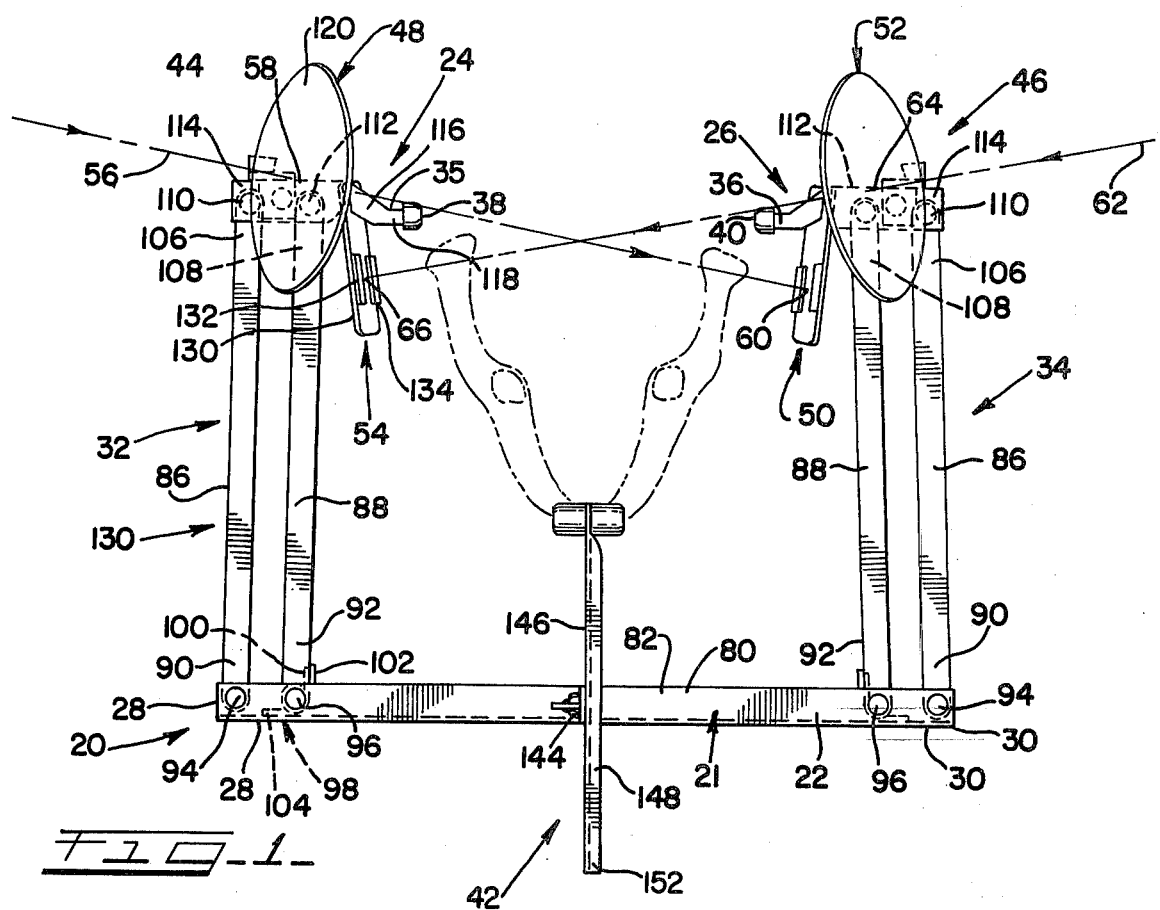
FIG. 1 is a plan view of one embodiment of the device showing it as it would be employed in operation, with portions of the human skull being shown in outline.

Referring first to FIGS. 4 and 5, the human jaw bone, indicated at 10, has a joint portion 12 on either side of the skull which is lodged in a socket 13 defined by the skull 14 to form what is known as the temporomandibular joint 16.

As has been indicated, it has been found that the TMJ 16 is subject to apparent minor dislocations, as for example, should normal occlusion be prevented by upstanding dental filling residue and the like that would preclude the upper and lower jaws from fully closing normally. Experience has shown that good diagnostic X-ray images of the TMJ will show when such minor misalignments and dislocations are or will occur due to occlusion obstructions, so that the dentist can make proper adjustments promptly and thereby avoid significant patient discomfiture that might otherwise be hard to diagnosis.

The devices 20 (FIGS. 1-3), 20A (FIG. 6), and 20B (FIGS. 7-10) are arranged to provide the practicing dentist with a ready way of making X-ray film images of the patient's TMJs while the patient remains seated in the dental chair, if desired, and using standard periapical size film that can be processed by standard dental film processing equipment and procedures This permits the dentist to have access to X-ray film images of a patient's TMJ articulations with the same speed and efficiency that he can obtain X-ray film images of the patient's teeth using conventional dental X-ray equipment.

Figure 2:
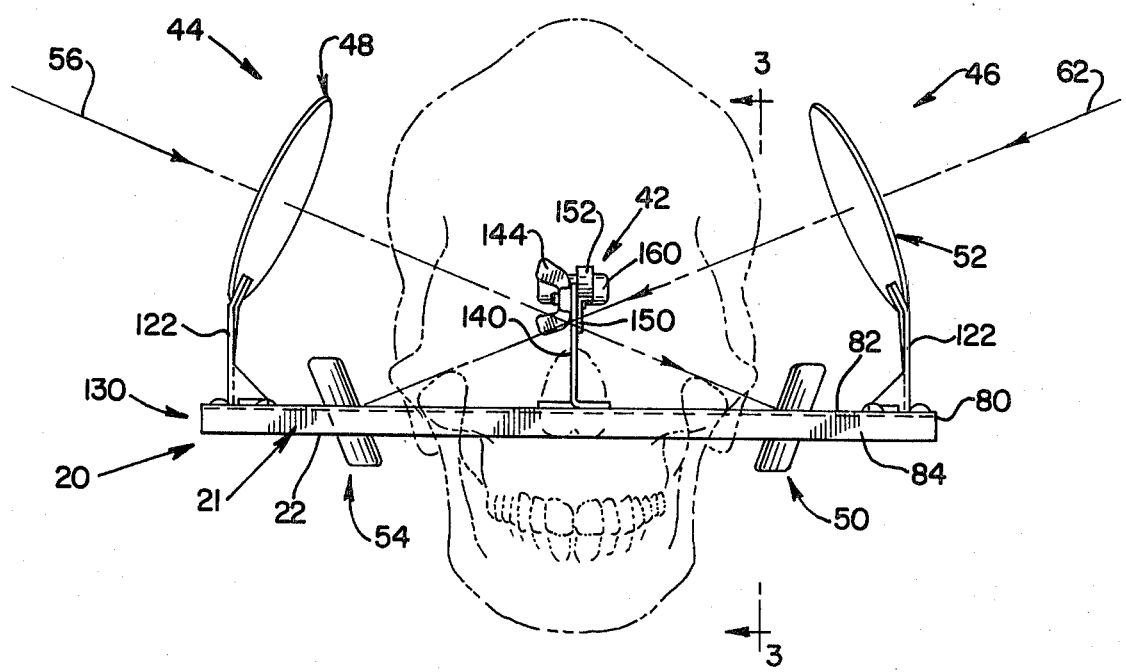
FIG. 2 is a front elevational view of the device as shown in FIG. 1, again showing the human skull in outline and as the device in use is to be positioned with respect thereto.

Referring first to the device 20 of FIGS. 1-3, the device 20 comprises (see FIGS. 1-3) a base portion 21 in the form of base member 22, having a pair of mounting members 24 and 26 articulated to the base member 22 at the ends 28 and 30 of the latter, by the respective sets of parallel linkages 32 and 34.

The mounting members 24 and 26 are disposed in substantial parallelism to the base member 22 and define opposed end portions 35 and 36 that are each equipped with the respective ear plug type applicators 38 and 40 that are proportioned to make a plug fit type application to the external auditary meatus of the patient's ears, in a manner similar to dictation transcribing equipment and the like.

The base member 22 is equipped with an adjustable nose rest indicated at 42 for supporting the base member 22 from the bridge of the patient's nose, and at a level in accordance with this invention.

A fundamental aspect of the invention is concerned with arranging the devices in question so that the film holder and X-ray axis to be directed to the film will be located, when the device employed is applied to the patient, with reference to a portion of the human head anatomy that may serve in the nature of a benchmark applicable to all patients for properly and reliably coordinating the film holder (and thus the film on which the image is to be formed) and the X-ray axis with the patient's TMJ to be radiographed, and on a basis that is consistently repeatable for re-X-raying at the same location at a later time or date. My studies of the subject have revealed that this may be done with reference to self locating parts of the human anatomy associated with the face and head. Referring to FIG. 4, indicated in broken lines are the human nose 21, including nostrils 23 and the Ala 25 of the nose (which is where the lower portions of the sides 27 of the nose meet the cheek 29 at what may be termed the Ala line 31). Also similarly indicated in FIG. 4 are the ear 33 and its Tragus 35 (which projects posteriorly over the entrance to the meatus 37).

In accordance with the invention, the film holder and the X-ray axis to be associated with same are coordinated with, for proper location with respect to the patient's TMJs, a plane 39 that connects the inferior portion of the Ala line 31 with the mid portion of the tragus 35. Plane 39, which may be called the Ala-tragal plane, and which intersects the exterior meatus 37, thus becomes the datum reference, that is readily established for each patient, with respect to which the X-ray coordinating devices of this invention are located, for effecting correct and restorable positioning relative to the TMJ to be radiographed.

The mounting members 24 and 26 are equipped with sets 44 and 46 of coordinated X-ray beam locating and film holder means. In the diagrammatically illustrated form of FIGS. 1-3, the set 44 comprises X-ray beam locater or positioner target 48 mounted on mounting member 24 and X-ray film holder 50 mounted on mounting member 26, while the set 46 comprises X-ray beam locating target 52 mounted on mounting member 26 and X-ray film holder 54 mounted on mounting member 24.

As to the radiographing set 44, the locating target 48 and the film holder 50 are disposed normally of and define X-ray axis 56 that may be assumed to be approximately aligned with the center points 58 and 60 of the target 48 and holder 50. The radiographic set 46 has its target 52 and holder 54 disposed normally of X-ray axis 62, which is assumed to be approximately aligned with the center points 64 and 66 of locater target 52 and film holder 54.

In accordance with the invention, the radiographic sets 44 and 46 are applied to the device 20 with such orientation and coordination that, when the device 20 is mounted on a patient's head in the manner indicated in the drawings, the X-ray axis 56 will pass through the patient's TMJ on the right side of his head while the X-ray axis 62 will pass through the patient's TMJ on the left side of the patient's head. Axes 56 and 62 are oblique to an imaginary straight line connecting the patient's joints 16, or a similar straight line connecting the patient's external auditory meatus (or external auditory canal) on either side of his head.

In accordance with this embodiment of the invention, the nose rest 42 supports the device 20 from the patient's nose, by adjusting same, to, together with the application applicators 38 and 40 to the patient's ears, so position device 20 that the radiographic sets 44 and 46 are positioned with respect to the Ala-tragal plane 39, so as to have the indicated orientation of axes 56 and 62 with respect to the patient's TMJS.

Furthermore, the mounting members 24 and 26 and the respective linkages 32 and 34 form parallel linkages whereby the mounting members 24 and 26 remain parallel to base member 22 as the members 24 and 26 are moved toward and away from each other so that the device 20 accommodates variations of patient head sizes and shapes without appreciably changing the coordination of the respective radiographic sets 44 and 46 and the respective X-ray axes 56 and 62.

Turning now more specifically to the specific details of construction of the embodiment illustrated in FIGS. 1-3, the mounting member 22 comprises in the form shown an elongate bar 80 that in the form shown is of right angled section (see FIG. 3) and thus defines main flange portion 82 and reinforcing flange portion 84 that is disposed normally of the flange portion 82.

The parallel linkages 32 and 34 each comprise a pair of parallel rectilinear links 86 and 88 pivotally connected to base member 22 at their ends 90 and 92 respectively, as by employing suitable connectors 94 and 96.

As it is desired that the mounting members 24 and 26 be spring biased toward each other so as to resist inadvertent dislodgement of the applicators 38 and 40 from the patient's ears, links 88 of the sets 32 and 34 each have applied to same the respective torsion wire springs 98 each having one arm 100 bearing against a tab 102 of the respective links 88 and a second arm 104 bearing against the reinforcing flange 84 of base member 22. The springs 98 are looped about the shanks of connectors 96 for convenience of application, which are headed as at 105 to retain springs 98 in place.

The links 86 and 88 at their ends 106 and 108 are pivotally connected to the respective mounting members by employing suitable connectors 110 and 112.

The mounting members 24 and 26 each comprise a planar body portion 114 to which the links 86 and 88 are pivotally connected, and a projecting neck portion 116 (forming the respective end portions 35 and 36 having at its end a tip portion 118 to which the respective applicators 38 and 40 are suitably secured. Applicators 38 and 40 are formed from a suitable plastic material or the like and are proportioned for snug fitting into the external auditary meatus of a patient. As a matter of practice applicators 38 and 40 within the ear when applied thereto may be comparable to conventional plug type elements that are on equipment of various known types that are applied to the external auditary meatus of a person's ears, such as stethoscopes, dictaphone transcribing equipment, and the like. In any event, in this embodiment they should be suitably perforated to avoid trapping of air within the ear when applied thereto due to the spring bias acting on linkages 32 and 34.

The X-ray locator targets 48 and 52 in the form illustrated each comprise a disc 120 formed from a suitable radiolucent plastic material (such as an acrylic plastic), and suitably secured by bonding or riveting to bracket members 122 that are in turn suitably secured to the mounting members 24 and 26, as by riveting or bonding. Alternately, targets 48 and 52 may be in the form of lead collimators, as in the device.

The film holders 50 and 54 each comprise a holder member 130 formed from a suitable plastic material and suitably bonded to the respective mounting members 24 and 26 in the positions indicated in the drawings. Holder members 130 are formed with the usual upper and lower holding flanges 132 and 134 for receiving the familiar dental X-ray film packet. The holding flanges 132 and 134 of the respective holders 50 and 54 shown are proportioned to receive and hold the familiar periapical film of appropriate size, though they may be replaced by suitable spring wire clips or the like.

In the illustrated embodiment, the discs 120 of locator targets 48 and 52 are 7.5 centimeters in diameter and are located approximately 6 centimeters from the respective applicators 38 and 40.

The film holder members 130 are 3.5 by 5 centimeter planar plastic elements (the size of a peripheral dental film packet).

It will be seen that base member 22, mounting members 24 and 26, and linkage sets 32 and 34 define a frame 130 that is generally planar in configuration, with the plane of the frame 130 being in parallelism with the main flange portion 82 of the base member 22.

In the form shown, with regard to the radiographing set 44, the locator target 48 and the holder 50, and specifically the disc 120 of target 48 and the holder member 130 of the film holder 50, are in parallel relation and they extend normally of the X-ray axis 56. These components are located so that the axis 56, when the device 20 is applied to a patient, will pass through the patient's TMJ on his left hand side, and for this purpose the target disc 120 and the film holder member 130 are angled such that their planes are angled at approximately 75 degrees relative to the plane of frame 130, and thus the Ala-tragal plane 39, and are disposed at an angle of approximately 75 degrees with respect to base member 22 and a straight line that is coaxial with the patient's external auditory meatus, as indicated in FIGS. 1 and 2.

With regard to the radiographing set 46 the relationship is similar but opposite, the disc 120 of locator target 52 and its related holder member 130 of film holder 54 being similarly inclined with respect to the plane of frame 130 and member 22, but disposed in opposite facing relation, as indicated in FIGS. 1 and 2.

The device 20 is arranged such that when applicators 38 and 40 are four and one quarter inches apart, axes 56 and 62 will be centered with respect to the respective radiographic sets 44 and 46. This dimension represents the average patient head size that will be encountered in practice; departure of the applicators 38 and 40 from this spacing up to about an inch in either direction can readily be accommodated by using an X-ray beam size that is slightly larger than the film employed.

Base member 22 is approximately 25 centimeters in length while links 86 and 88 are approximately 17 centimeters in length. The mounting members 24 and 26 are approximately 6 centimeters in length.

With the proportion and angling of parts that are indicated, when a device 20 is applied to a patient's head in the manner indicated in the drawings, the X-ray axis 56 will pass through the patient's left side TMJ, while the axis 62 will pass through the patient's right side TMJ.

The nose rest 42 comprises a pedestal 140 disposed at the mid portion of base member 22 and in perpendicular relation thereto to which is applied headed stud 142 suitably threaded for application thereto of wing nut 144. Mounted on the stud 142 for lost motion movement therewith is nose rest member or strut 146 in the form of elongate element 148 of right angled transverse cross-sectional configuration defining main flange portion 150 and brace flange portion 152, with the flange portion 150 being formed to define elongate slot 154 which is received over the stud 142 behind its headed end 156. Support member 146 is formed to define a headed end 158 to which is suitably secured a rounded foot 160 of double ended configuration.

The support member or strut 146 serves the function of forming a supporting prop for supporting the base member end of frame 130 from the bridge of the patient's nose, when the applicators 34 and 36 have been applied to the patient's ears. The proportioning and arrangement of the nose rest 42 is such that when the frame 130 has been applied to the patient's ears, as by applying the applicators 38 and 40 to the patient's external auditary meatus on either side of his head, the foot rest 42 may be adjusted to bring the foot 160 into supporting relation with the bridge of the patient's nose such that the plane of the frame 130 will be approximately aligned with the patient's Ala-tragal plane 39 (as indicated in FIGS. 2 and 3). This is done by the dentist adjusting foot rest 42 so that the frame 130 is approximately aligned with Ala of the nose at the level of Ala line 31; the portion of frame 130 at the area of applicators 34 and 40 is automatically properly oriented with plane 39 since plane 39 passes through the meatus 37. With this positioning of the parts, the X-ray axes 56 and 62 will be properly oriented for X-raying the patient's TMJ articulations.

For this purpose, the wing nut 144 is loosened and support member 146 adjusted positionally with respect to the base member 22 to achieve the positioning indicated in FIGS. 2 and 3 with respect to the patient's head whereupon the wing nut 144 is tightened to hold the nose rest components in adjusted position.

Film appropriate for use in connection with device 20 is preferably prepared in the familiar conventional packets each containing a sheet of appropriate X-ray film of periapical size (such as the so called medical film), having a suitable type of light intensifying film screen on either side of same for minimumizing needed exposure time, because of potential patient movement during exposure, and to minimize radiation exposure. In this connection, the type of film and intensifying screens employed for any application should be that which yields the best detail with the least exposure time.

The device is used by applying the applicators 34 and 36 of the respective mounting members 24 and 26 to the patient's ears in the manner already indicated, the linkages 32 and 34 being articulated as necessary to apply the frame 130 to the patient's head as may be necessary by the particular sizing and shape of the head of the patient involved. The nose rest 42 is then manipulated to dispose the frame 130 in alignment with the patient's Ala-tragal plane 39. The patient is then ready for X-raying of his left and right TMJ articulations, with the radiographic sets 44 and 46 being alternately used for this purpose, their respective holders 50 and 54 being supplied with X-ray film packets of the type indicated as needed.

As will be apparent, the device 20 may be applied and used while the patient sits in a normal upright position in the dental chair or other location of the dentist's standard X-ray equipment. Of course, the patient may stand upright for this purpose if that is appropriate under the circumstances of given X-ray set up. The PID or cone of the X-ray machine may then be successively aligned with the respective X-ray axes 56 and 62 and the film exposed accordingly for processing development in the usual manner customary with dental film. In this connection, the X-ray machine PID or cone is disposed in perpendicular relation with the planes of the respective locator targets 48 and 52, in centered relation therewith, for alignment with the respective X-ray axes 56 and 62.

The exposed film may then be promptly processed for analyzation of the patient's TMJ articulations and prompt modification of the occlusal surfaces of the teeth, as may be deemed adviseable by the TMJ articulation images so produced. By reapplying device 20 to the patient in the manner indicated, the patient's TMJs may again be radiographed with the same X-ray axis orientation as initially radiographed, for final checking of occlusion.

It will be apparent, of course, that the disc type locators 48 and 52 may be replaced by ring type locating or positioning elements that are in common use in connection with dental X-ray instrumentation. Also, the film packets may be applied to or removed from device 20 while device 20 remains in operating position on the patient's head.

Referring now to FIG. 6, the device 20A comprises frame 130A in which the base member 22A is of bar configuration defining at either end of same a pair of oppositely directed elongate slots 170 and 172 that are open at their respective ends 174 and 176 to receive the respective slotted lugs 178 and 180 of the base portions 182 and 184 of the respective arms 186 and 188 that take the place of the respective linkages 32 and 34. The respective lugs 178 and 180 are slidably mounted in the respective slots 174 and 176 for movement longitudinally thereof, they being spring biased to spring bias arms 186 and 188 toward each other by suitable coil spring 190 connected to the respective lugs at 192 and 194, respectively, on the underside of member 22A.

The mounting members 24 and 26 of the embodiment of FIGS. 1–3 are suitably affixed to the projecting ends of the arms 186 and 188 to provide the radiographic sets 44 and 46 described in connection with the device 20. Device 20A is also provided with the foot rest 42 that is omitted from the showing of FIG. 6.

The device 20A is employed in the same manner as the device 20, with the arms 186 and 188 being separated from each other against the bias of spring 190 to apply and remove the device 20A.

The device 20B of FIGS. 7–10 is arranged to provide a different three point type support on the patient's head whereby the device is braced against the top of the patient's head, rather than on the patient's nose, in addition to the application of the device to the patient's external auditory meatus.

The device 20B comprises the sets 44B and 46B of coordinated X-ray beam locating and film holder means, comparable to the corresponding sets 44 and 46 of the embodiments of FIGS. 1–6. Thus, the set 44B comprises X-ray beam locator or positioner target 48B secured to mounting member 24B and X-ray film holder 50B suitably mounted on mounting member 26B, while the set 46B comprises X-ray beam locater 52B mounted on mounting member 26B and X-ray film holder 54B mounted on the mounting member 24B. The mounting member 24B and 26B are provided with the aforedescribed applicators 38 and 40.

The locators 48B and 52B in the form shown each comprise a ring member 200 suitably mounting a collimator plate 202 formed at its mid portion to define the usual window opening 204 that is shaped to limit the size of the X-ray beam to be projected therethrough to a size approximating but slightly larger than the size of the film employed. Plates 202 are formed from lead, as is the practice for collimators.

The locater 48B is affixed to holder arm 208 having a rectilinear portion 210 at approximately right angles with respect thereto for sliding engagement with corresponding rectilinear portion 212 of holder arm 209 on which locater 52B is affixed.

The holder arm portions 210 and 212 are slotted longitudinally thereof as at 213 and 215 (see FIG. 10) and receive the shanks of screws 214 and 216 that extend through clamp plate 218 and the respective bar portions 212 and 210 for application to suitable nuts 220 and 222 to lock the legs 208 and 210, and thus the applicators 38 and 40 of the device 20B at a desired distance between the applicators 38 and 40. The screw 214 and its nut 220 forms fastener device 217 while the screw 216 and its nut 222 forms fastener device 219. Devices 217 and 219 are suitably positioned so that holder arm portions 210 and 212 are frictionally held against relative shifting movement, but can be readily shifted relative to each other by the operator suitably grasping the arms 208 and 209 and moving them toward or away from each other, as needed.

Carried by the clamp bar 218 is a head rest device 230 comprising a rest pad 232 secured to the end of holder rod 234 that extends through slots 213 and 215 to and through collet body 236 that is suitably secured to clamp plate 218 in the manner indicated in FIG. 7A.

The collet body 236 is of the usual split configuration externally threaded for cooperation with collet nut 238 for releasably clamping the collet body 236 against the rod 234 at a desired position of adjustment of the rest 232 with respect to the holder arms 208 and 210. Collet body 236 and its nut 231 form collet device 239 for holding head rest at a desired position of adjustment. Rod 234 is equipped with hand grip handle 237 for moving rod 234 when collet device 239 is released.

The film holders 50B and 54B are suitably arranged to hold the indicated film packets. In the form shown they comprise a body 240 having a single lower holding plate 242 suitably affixed thereto (as by bonding) and spaced from the respective bodies 240 to define the respective slots 241 that receive the individual film packets. Of course, the plates 242 may be replaced by suitable spring wire clips or the like, or the holders 50B and 54B may be the same as holders 50 and 54.

The holder arms 208 and 209 form a frame 130B that defines an adjustable bridge portion 250 which receives the patient's head in the use of the device, in which the component parts thereof including the head rest device 230 are in coplanar relation, as indicated in FIG. 8. Holder arms 208 and 209 are angled to provide the angulation of the locaters 48B and 52B that is the same as the angulation of the locaters 48 and 52 of the device 20. Similarly, the film holders 50B and 54B are angled in the same manner as film holders 50 and 54.

The frame 130B adjacent one of the mounting members 24B or 26B (member 26B in the illustrated embodiment) has secured thereto an indicator arm 260, which, as indicated in FIG. 10, has a projecting end portion 262 which is intended to be employed for locating the device 20B with respect to the patient's Ala-tragal plane 39, in the manner indicated in FIG. 9. For this purpose, the indicator arm 260 is angled as at 264 and is pivotally connected to the frame 130B, as at 266, with a friction type pivot action being preferred.

The locators 48B and 52B each have associated therewith the respective aiming members 270 and 272, for facilitating alignment of the X-ray machine PID or cone with the respective locators 48B and 52B. The members 270 and 272 are each shown in the form of a rod 274 having plastic end piece 276 and suitably secured to their respective holder members 208 and 209. Member 270 parallels axis 56 while member 272 parallels axis 62. Rods 276 may alternately be in the form of pretensioned coil springs for flexibly yielding if accidentally bumped by the operator when positioning the X-ray PID relative to the respective locators.

In utilizing the device 20B, assuming the patient has been readied for application of the device to the patient, the frame 130B is adjusted by shifting and disposing the holder arms 208 and 209 relative to each other as needed to apply the device to the patient's head, with the applicators 38 and 40 comfortably seated in the patient's ears. The frame 130B is then pivoted about the axis represented by the imaginary line connecting the patient's external auditory meatus on either side of his head to bring the end portion 262 of indicating arm 260 into approximate alignment with the patient's Ala line 31, and specifically with the inferior portion of same. The arm 260 may be pivoted about its pivotal mounting to dispose its end portion 262 in close proximity with the patient's face, as needed, to do this. With the operator then holding the frame 130B as so positioned with respect to the Ala-tragal plane 39, head rest 232 is lowered against the patient's head in supporting relation thereto, with sufficient pressure to hold the device 20B in place, and then secured in place by operating collet nut 238.

In this connection, it is pointed out that the applicators 38 and 40 of this embodiment need not be perforated, as no spring loading is involved in their fitting to the patient's ears, and sufficient upward force is generated by the action of the head rest 232 bearing on the patient's head to vent the ears.

The device 20B is now positioned for X-raying of the patient's TMJs, following the procedures previously described.

The device 20B is quickly removed from the patient by swinging the indicator arm 260 away from the patient's face, shifting the head rest 232 upwardly, and separating the holder arms 208 and 209 as necessary to separate the applicators 38 and 40 from each other for ready removal of the device 20B from the patient's head.

For retaking of the patient's TMJs, the device 20B is reapplied to the patient in the same manner as previously described for a retaking of the desired X-rays under the same positioning and conditions as the first set of TMJ X-rays, the indicator arm 260 alignment with Ala line 31 supplying the datum reference needed to return the device 20B to the same positioning it had for the initial set of TMJ radiographs.

In all of the devices illustrated, it is preferred that the film holders employed be mounted on the devices so that when the device in question is aligned with the patient's Ala-tragal plane, the film holders will be more or less centered with respect to such plane. It is preferred that in practice the centers of the film holders employed be approximately ⅛th of an inch above the level of the indicated plane 39. As indicated, it is preferred that appropriate film (such as the so called medical film) conventionally packaged in individual packets with intensifying screens, be used in using the disclosed devices as film of this type is 80 percent exposed by fluorescent light from the screens and 20 percent exposed by X-ray, as compared to regular dental film being 100 percent exposed by X-ray. When film of the type indicated is prepackaged to have an intensifying screen on either side of same, in a conventional manner, film exposure is fast enough to avoid patient movement that could adversely affect the desired film image, and patient radiation exposure is kept to a minimum.

It will therefore be seen that the invention provides a device for making X-ray film images of TMJ articulations that has a number of significant advantages.

For instance, the operation of the device is very simple and requires no special training on the part of the user. The X-ray generating equipment may be and preferably is one of the types now in common use by dentists for making dental X-ray images.

The device may be employed while the patient remains in a normal upright sitting or standing position, and since the device is mounted on the patient's head, the X-ray exposures can be made in any head position as the device will move with it.

The positioning and orientation of the components of the device are arranged for precise application of the X-ray beams to the respective TMJ articulations of the patient and provide a repeatable reference for future exposures of equal prospective and dimension. The exposures can be taken in any desired occlusal contact of the teeth because the mounting of the device on the patient's head permits full access to the oral cavity. The device avoids the need for special equipment formerly required for making TMJ X-rays, including both the x-ray taking equipment and special equipment and office space for processing the films. As the device contemplates the use of medical film of standard dental film size, exposure and development time will be comparable to that expected for dental film. Furthermore, the finalized films can be mounted and stored by using regular dental film mounts.

The device and method provided by the invention give the dentist the ability to define "ideal" condyle positions in temporal fossa, and the ability to coordinate occlusion of the teeth with "ideal" TMJ relationships as well as to verify such relationships. The device also provides the ability to control target exposure to a minimum area on the order of 2½ inches in diameter using lead collimators in the beam locators, as herein disclosed.

In the area of general denistry, the device permits routine diagnostic procedures with regard to TMJ syndromes and incorrect occlusal relationships. Also, in using the device ready access to the oral cavity is permitted, so that positions of the patient's TMJ's as related to various desired relationships of the patient's upper and lower teeth can be compared and analyzed in a given series of X-rays. Other applications of the device and resulting benefits will be obvious to those skilled in the dental arts.

The foregoing description and the drawings are given merely to explain and illustrate the invention and the invention is not to be limited thereto, except insofar as the appended claims are so limited, since those skilled in the art who have the disclosure before them will be able to make modifications and variations therein without departing from the scope of the invention.

I claim:

1. A radiographing device adapted for application to a patient's head for mounting on and support thereby for radiographing the patient's jaw joints, said device comprising:
    a frame including:
    a pair of opposed end portions positioned to be disposed one on either side of the patient's head and each including plug fit means for making plug fit relation with patient's ears for pivotally mounting the frame on the patient's head for pivotal movement about a pivot axis extending between the patient's ears,
    said frame carrying a film holder and an X-ray beam locator,
    said holder and locator being spaced apart to receive the patient's head therebetween and being disposed in substantial parallelism and aligned with a common radiographing axis extending normally of same,
    said holder and locator being oriented on said frame such that in one position of adjustment of said frame about said pivot axis, said common radiographing axis passes through the patient's jaw joint to be radiographed,
    said frame including releasable holding means for engaging the patient's head at a point spaced from said pivot axis to releasably hold said frame at said position of adjustment against movement about said pivot axis relative to the patient's head, for radiographing of the patient's jaw joint to be radiographed.

2. The device set forth in claim 1 including:

means for coordinating said holder and said locator with the patient's Ala-Tragal plane including indicating means that aligns with the patient's Ala-Tragal plane at said one position of adjustment of said frame about said pivot axis.

3. The device set forth in claim 2 wherein said indicating means comprises:

said frame being of planar configuration, and wherein said holding means comprises means for supporting said frame on the patient's nose to dispose said frame in substantial alignment with the patient's Ala-Tragal plane.

4. The device set forth in claim 2 wherein:

said frame includes an indicating arm substantially coplanar with said frame end portions and having a projecting end portion oriented for alignment with the Ala of the patient's nose and comprising said coordinating means.

5. The device set forth in claim 4 wherein:

said frame includes a bridge portion for overlying the patient's head when said frame is said one position of said frame, said holding means including means for bracing said frame bridge portion against the patient's head.

6. The device set forth in claim 5 wherein:

said bracing means comprises:

a seat adapted to engage the top of the patient's head, and means for adjusting said seat toward and away from said frame bridge portion.

7. A radiographing device adapted for application to a patient's head for mounting on and support thereby for radiographing the patient's jaw joints, said device comprising:

a frame including:

a pair of mounting members positioned to be disposed one on either side of the patient's head and defining opposed end portions, each including plug fit means for making plug fit relation with patient's ears for pivotally mounting the frame on the patient's head for pivotal movement about a pivot axis extending between the patient's ears, one of said mounting members carrying a film holder and the other of said mounting members carrying an X-ray beam locator, said holder and locator being spaced apart to receive the patient's head therebetween and being disposed in substantial parallelism and aligned with a common radiographing axis extending normally of same, said holder and locator being oriented on said frame such that in one position of adjustment of said frame about said pivot axis, said common radiographing axis passes through the patient's jaw joint to be radiographed, said frame including bracing means for engaging the patient's head at a point spaced from said pivot axis to releasably hold said frame at said position of adjustment against movement about said pivot axis relative to the patient's head, for radiograping of the patient's jaw joint to be radiographed.

8. The device set forth in claim 7 wherein:

said mounting members are mounted for adjustment toward and away from each other for accommodating variations in patient head size.

9. The device set forth in claim 7 wherein:

the other of said mounting members carries a second film holder and said one mounting member carries a second X-ray beam locator, said second holder and said second locator being in substantial parallelism and aligned with a second common radiographing axis extending normally of same, said second holder and said second locator being oriented on said frame such that in said one position of adjustment of said frame about said pivot axis, said second common radiographing axis passes through the patient's other jaw joint for radiographing of same.

10. The device set forth in claim 7 including:

means for coordinating said holder and said locator with the patient's Ala-Tragal plane including indicating means that aligns with the patient's Ala-Tragal plane at said one position of adjustment of said frame about said pivot axis.

11. The device set forth in claim 10 wherein said frame further comprises:

an elongate base member defining opposite end portions at either end of same, said mounting members being disposed on one side of said base member, first arm means for connecting one of said mounting members to one end portion of said base member, second arm means for connecting the other of said mounting members to the other end portion of said base member, said arm means being of substantially equal lengths and disposing said members in substantial coplanar relation, said bracing means comprising an adjustable nose rest mounted on said base member for resting that end of said frame on the patient's nose in alignment with the Ala of the patient's nose at said one position of adjustment of said frame, whereby said frame comprises said coordinating means.

12. The device set forth in claim 11 wherein:

said arm means of the respective mounting members are spring biased to move said mounting members toward each other.

13. A method of radiographing one of the jaw joints of a human patient's head to form an image of the joint on an X-ray film, said method comprising:

positioning the patient in an upright position, and while the patient remains positioned in an upright position, mounting on the patient's head and supporting therefrom an X-ray beam locator and the film one on either side of the patient's head and disposed in a substantially parallel relationship in which the locator and the film are positionally fixed with respect to each other and are aligned with a common radiographing axis extending normally of the locator and film and oblique to the straight line connecting the external auditory canals of the patient's ears, adjusting the locator and film about said straight line as a pivot axis to dispose the locator and the film in a radiographing position in which said common radiographing axis passes through the patient's jaw joint to be radiographed.

fixing the locator and film relative to the patient's head in said radiographing position thereof, and directing an X-ray beam from an X-ray source along said radiographing axis through the locator and against the film.

14. The method set forth in claim 13 wherein:

said locator and the film are positionally coordinated with the patient's Ala-Tragal plane for operably establishing said radiographing position of the film as the correct radiographing position of the film relative to the jaw joint to be radiographed.

15. The method set forth in claim 14 wherein: the film is medical film overlaid with light intensifying screens.

16. The method set forth in claim 14 wherein: the film is periapical size film.

17. The method set forth in claim 14 wherein: the radiographed jaw joint is subsequently reradiographed on a new X-ray film practicing said steps of claim 14 utilizing the new film in place of the radiographed film for providing a second film bearing an image of the joint with perspective and dimension equal to that of the first film image.

* * * * *